United States Patent [19]

Eckhardt

[11] 4,187,289

[45] Feb. 5, 1980

[54] SOFTENING AGENTS CONTAINING DIESTER/AMINE ADDUCTS AND QUATERNARY AMMONIUM SALTS, VALUABLE FOR USE AS AFTER-RINSE SOFTENERS AND AFTER-SHAMPOO HAIR CONDITIONERS

[75] Inventor: Claude Eckhardt, Riedisheim, France

[73] Assignee: Ciba-Geigy Corporation, Ardsley, N.Y.

[21] Appl. No.: 853,067

[22] Filed: Nov. 21, 1977

[30] Foreign Application Priority Data

Dec. 3, 1976 [CH] Switzerland .................. 15255/76

[51] Int. Cl.² .......................... A61K 7/06; A61K 7/08
[52] U.S. Cl. ................................. 424/70; 8/127.51; 8/127.6; 8/128 R; 8/188; 8/189; 252/8.8
[58] Field of Search ............... 424/70; 252/8.8; 8/188, 8/189, 127.51, 127.6, 128

[56] References Cited

U.S. PATENT DOCUMENTS

| | | | |
|---|---|---|---|
| 3,822,312 | 7/1974 | Sato et al. | 424/70 X |
| 3,954,630 | 5/1976 | Ramachandran | 252/8.8 |
| 3,954,634 | 5/1976 | Monson et al. | 252/8.8 |
| 3,956,243 | 5/1976 | Loss et al. | 252/8.8 |
| 3,979,442 | 9/1976 | Schafer et al. | 252/8.8 |

Primary Examiner—Bernard Helfin
Assistant Examiner—Vera C. Clarke
Attorney, Agent, or Firm—Prabodh I. Almaula

[57] ABSTRACT

A softening agent is provided which contains
(a) a diester/amine adduct of the formula

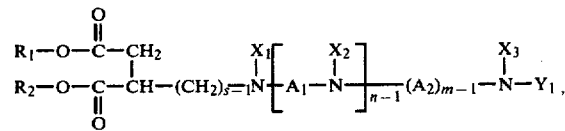

in which $X_1$, $X_2$ and $X_3$ are —H, 1–4 C alkyl, 2–4 C hydroxyalkyl or hydroxyhalogenalkyl or

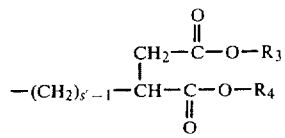

$Y_1$ is 1–4 C alkyl or

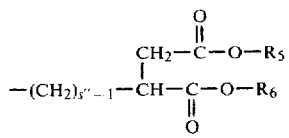

$R_1$, $R_2$, $R_3$, $R_4$, $R_5$ and $R_6$ are 12–22 C alkyl or alkenyl,
$A_1$ and $A_2$ are 2–3 C alkylene or 2-hydroxy-n-propylene
m, s, s' and s'' are 1 or 2 and
n is 1, 2, 3 or 4, and
(b) a quaternary ammonium salt of the formula

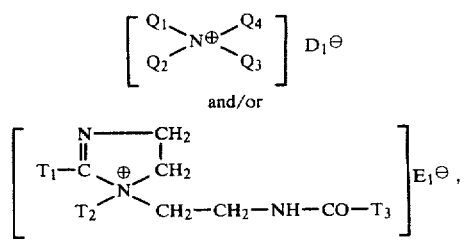

in which
$Q_1$ and $T_2$ are —H, 1–8 C alkyl or 2–8 C alkenyl,
$Q_2$ is 1–8 C alkyl or 2–8 C alkenyl,
$Q_3$, $T_1$ and $T_3$ are 8–30 C alkyl or alkenyl,
$Q_4$ is 1–30 C alkyl or 2–30 C alkenyl and
$D_1^\ominus$ and $E_1^\ominus$ are an anion imparting water-solubility or water-dispersability.

These softening agent are valuable for use as after-rinse softeners and hair-conditioners.

16 Claims, No Drawings

SOFTENING AGENTS CONTAINING DIESTER/AMINE ADDUCTS AND QUATERNARY AMMONIUM SALTS, VALUABLE FOR USE AS AFTER-RINSE SOFTENERS AND AFTER-SHAMPOO HAIR CONDITIONERS

The invention relates to a softening agent which contains (a) a diester/amine adduct of the formula

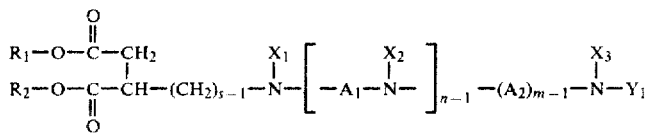

wherein each of $R_1$ and $R_2$ represents alkyl or alkenyl of 12 to 22 carbon atoms, each of m and s is 1 to 2 and n is 1, 2, 3 or 4, each of $A_1$ and $A_2$ represents alkylene of 2 or 3 carbon atoms or 2-hydroxy-n-propylene, each of $X_1$, $X_2$ and $X_3$ represents hydrogen, alkyl of 1 to 4 carbon atoms, hydroxyalkyl or hydroxy-halogenalkyl of 2 to 4 carbon atoms or a radical of the formula

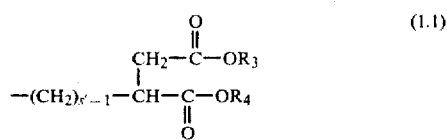

in which each of $R_3$ and $R_4$ represents alkyl or alkenyl of 12 to 22 carbon atoms and s' is 1 or 2, with the proviso that, if n is 3 or 4, the individual radicals $X_2$ are the same or different and $Y_1$ represents hydrogen, alkyl of 1 to 4 carbon atoms or a radical of the formula

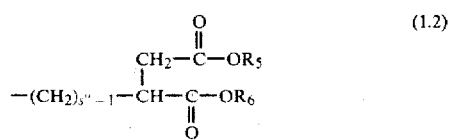

in which each of $R_5$ and $R_6$ represents alkyl or alkenyl of 12 to 22 carbon atoms and s'' is 1 to 2, and the ratio of the diester groups to the nitrogen atoms is 1:1 and the adduct of the indicated formula is in the form of the free base, acid salt or quaternary ammonium salt; and (b) at least one quaternary ammonium salt of the formula

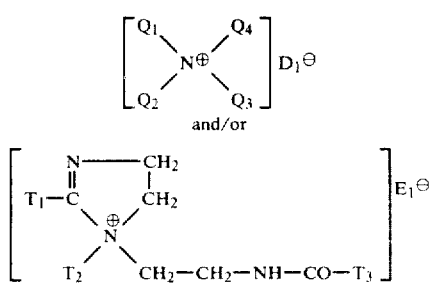

wherein each of $Q_1$ and $T_2$ represents hydrogen, alkyl or alkenyl of not more than 8 carbon atoms, $Q_2$ represents alkyl or alkenyl of not more than 8 carbon atoms, each of $Q_3$, $T_1$ and $T_3$ represents alkyl or alkenyl of 8 to 30 carbon atoms, $Q_4$ represents alkyl or alkenyl of not more than 30 carbon atoms. and each of $D_1^\ominus$ and $E_1^\ominus$ represents an anion which imparts water-solubility or water-dispersibility to the ammonium salts, the weight ratio of diester/amine adduct to ammonium salts being 9.5:0.5 to 1:9.

As a rule, each nitrogen atom of the diester/amine adduct of the formula (1) contained as component (a) in the softening agent of the invention carries only not more than 1 diester group of the formula (1.1) or (1.2).

Accordingly, $X_1$ in formula (1) preferably does not represent a diester group of the formula (1.1). Likewise, $X_3$ in formula (1) preferably does not represent a diester group of the formula (1.1), provided $Y_1$ itself corresponds to a diester group of the formula (1.2).

Preferably, component (a) is a diester/amine adduct of the formula

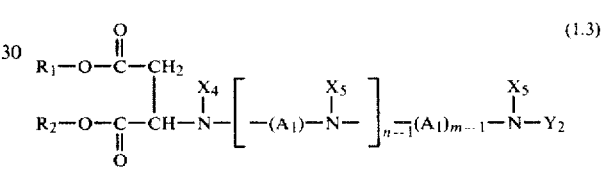

wherein each of $R_1$ and $R_2$ represents alkyl or alkenyl of 12 to 22 carbon atoms, m is 1 or 2 and n is an integer from 1 to 4, $A_1$ represents alkylene of 2 or 3 carbon atoms or 2-hydroxy-n-propylene, each of $X_4$ and $X_5$ represents hydrogen, alkyl of 1 to 4 carbon atoms, hydroxyalkyl or hydroxy-halogenalkyl of 2 to 4 carbon atoms, $Y_2$ represents alkyl of 1 to 4 carbon atoms or a radical of the formula

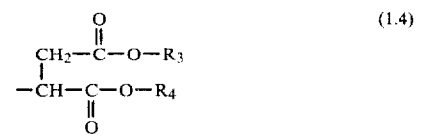

wherein each of $R_3$ and $R_4$ represents alkyl or alkenyl of 12 to 22 carbon atoms, said adduct being in the form of a free base, acid salt or quaternary ammonium salt.

A further preferred component (a) is an adduct of the formula

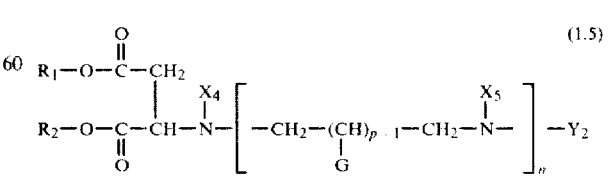

wherein G represents hydroxyl or, in particular, hydrogen, and p is 1 or 2, and $R_1$, $R_2$, $X_4$, $X_5$, $Y_2$ and n have the given meanings.

Accordingly, $A_1$ and $A_2$ preferably represent a 2-hydroxy-n-propylene or, in particular, an ethylene or propylene radical.

A particularly preferred component (a) has the formula

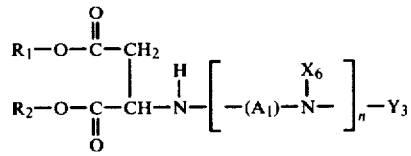
(1.6)

wherein $R_1$, $R_2$, $A_1$ and n have the given meanings, $X_6$ represents hydrogen or alkyl of 1 or 2 carbon atoms and $Y_3$ represents alkyl of 1 or 2 carbon atoms or a radical of the formula (1.4), and, in particular, has the formula

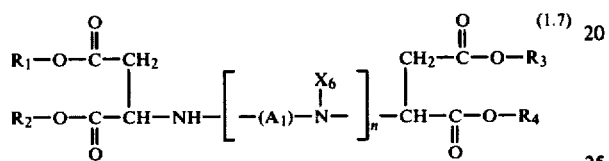
(1.7)

wherein $R_1$, $R_2$, $R_3$, $R_4$, $A_1$, $X_6$ and n have the given meanings.

Alkyl represented by $X_1$, $X_2$, $X_3$, $X_4$, $X_5$ and $X_6$ is for example n-butyl, tert-butyl, isopropyl, n-propyl and, in particular, ethyl or methyl.

Hydroxyalkyl in the definition of $X_1$, $X_2$, $X_3$, $X_4$ and $X_5$ is for example 2-hydroxyethyl or 4-hydroxy-n-butyl. Preferably, the symbols $X_1$, $X_2$, $X_4$, $X_5$ and $X_6$ represent methyl or, in particular, hydrogen.

Alkyl represented by $Y_1$, $Y_2$ and $Y_3$ can have the same meaning as given for $X_1$, $X_2$, $X_3$, $X_4$, $X_5$ and $X_6$.

Particularly interesting diester/amine adducts are those of the formula

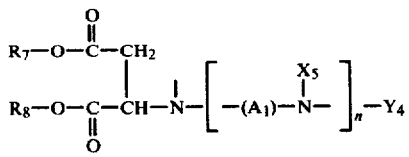
(1.8)

wherein $A_1$, $X_5$ and n have the given meanings, each of $R_7$ and $R_8$ represents alkyl or alkenyl of 16 to 18 carbon atoms and $Y_4$ represents methyl, ethyl or a radical of the formula

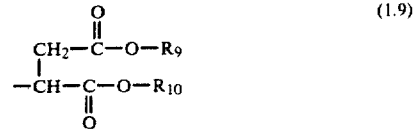
(1.9)

wherein each of $R_9$ and $R_{10}$ represents alkyl or alkenyl of 16 to 18 carbon atoms.

$R_1$, $R_2$, $R_3$, $R_4$, $R_5$ and $R_6$ and $R_7$, $R_8$, $R_9$, and $R_{10}$ are preferably radicals which are derived from branched or unbranched, saturated or ethylenically unsaturated aliphatic alcohols. For example they can be dodecyl, tridecyl, myristyl, cetyl, behenyl or, in particular, stearyl or oleyl. The radicals $R_1$ to $R_6$ and $R_7$ to $R_{10}$ can the same or different.

Particularly suitable diester/amine adducts which can be used as component (a) are also those of the formula

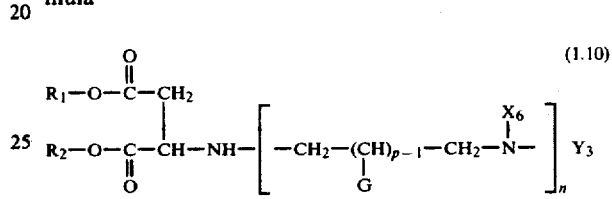
(1.10)

or, in particular, those of the formula

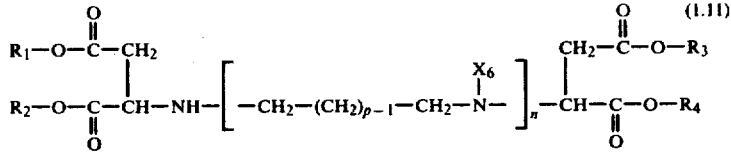
(1.11)

wherein $R_1$, $R_2$, $R_3$, $R_4$, $X_6$, $Y_3$, G, n and p have the given meanings.

As already mentioned, the adducts of the formulae (1) to (1.11) can be in the form of free bases, acid salts or quaternary ammonium salts.

The conversion of the basic adducts into the acid salts is accomplished by taking up the adducts in water and neutralising with acids. Suitable acids for this purpose are, for example, hydroxyalkyl- or alkylcarboxylic acids of 1 to 3 carbon atoms or a diester of phosphorous acid, such as lactic acid, dimethyl phosphite or, in particular, formic acid or acetic acid.

The acid salts are preferred to the free bases and the quaternary ammonium salts.

The quaternary ammonium salts are obtained by quaternising adducts containing tertiary nitrogen atoms with conventional quaternising agents, such as alkyl halides or dialkyl sulphates, for example methylene chloride, dimethyl sulphate or diethyl sulphate.

The most preferred component (a) of the softening agent of the present invention is an adduct of the formula

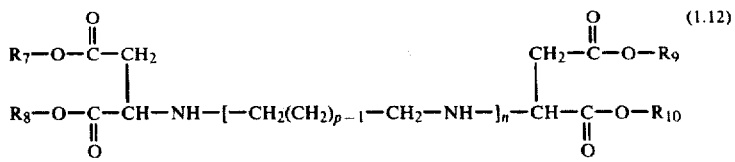
(1.12)

wherein $R_7$, $R_8$, $R_9$, $R_{10}$, n and p have the given meanings, said adduct being in the form of an acid salt, in particular an acid salt of acids of the indicated kind.

Accordingly, of preeminent interest as component (a) is an adduct of the formula

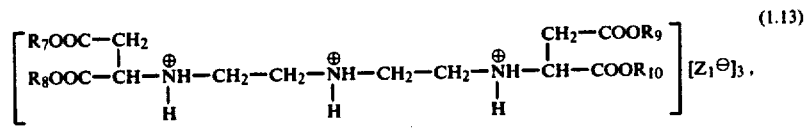

(1.13)

and, in particular, of the formula

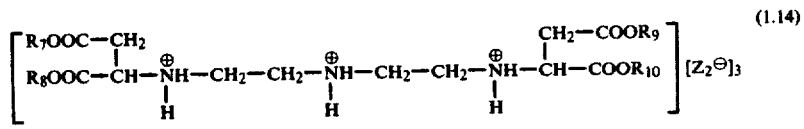

(1.14)

wherein $Z_1$ represents the radical of an acid having reductive character and $Z_2^\ominus$ represents $CH_3COO^\ominus$ or $HCOO^\ominus$ and $R_7$, $R_8$, $R_9$, and $R_{10}$ have the given meanings.

The diester/amine adducts used as component (a) in the softening agents of the present invention are known per se and are prepared by methods which are commonly known in the art. These adducts and the processes by which they are obtained are described for example in British patent specification No. 1,419,154.

As examples of specific types of compound of the formulae (1) to (1.4), the compounds of one of the following formulae may be cited:

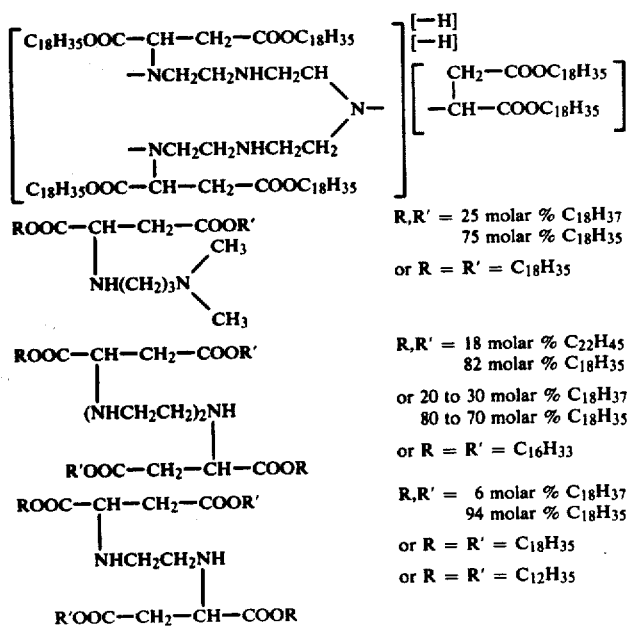

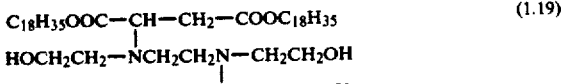

(1.19)

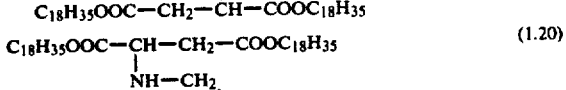

(1.20)

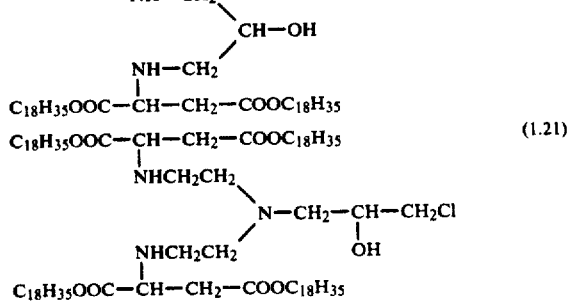

(1.21)

-continued

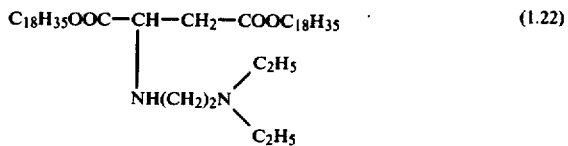
(1.22)

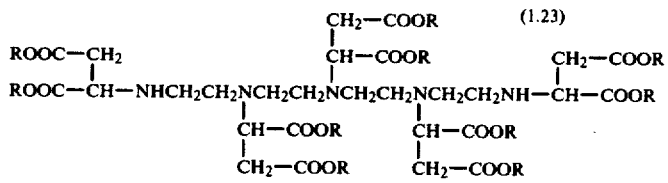
(1.23)

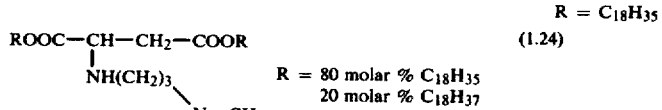
(1.24)

R = C₁₈H₃₅
R = 80 molar % C₁₈H₃₅
20 molar % C₁₈H₃₇

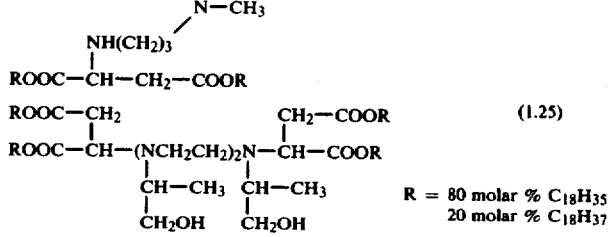
(1.25)

R = 80 molar % C₁₈H₃₅
20 molar % C₁₈H₃₇

In particular, the acid salts of the compounds of the formulae (1.15) to (1.25) are especially preferred, most particularly the salt of the formula

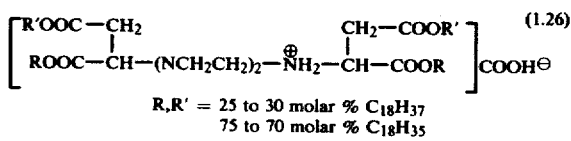
(1.26)

R,R' = 25 to 30 molar % C₁₈H₃₇
75 to 70 molar % C₁₈H₃₅

Mixtures of compounds of the formulae (1) to (1.26) are also suitable for use as component (a) of the softening agent of the present invention.

Component (b) of the softening agent of the present invention is a quaternary ammonium salt which consists of a mixture of the compounds of the formulae (2) and (3), or preferably of the compound of the formula (2) or the compound of the formula (3). The compound of the formula (2) is preferred to the compound of the formula (3).

Preferred embodiments of the aliphatic quaternary ammonium salts of the formula (2) have the formula

(2.1)

wherein $D_2^{\ominus}$ represents the amine of a hydrohalic acid, of a dialkyl sulphate containing 1 or 2 carbon atoms in the alkyl moiety, or of an alkylcarboxylic acid of 1 to 4 carbon atoms, and $Q_1$, $Q_2$, $Q_3$ and $Q_4$ have the given meanings, and in particular have the formula

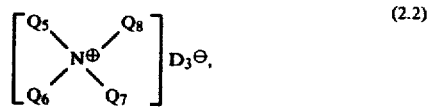
(2.2)

wherein each of $Q_5$ and $Q_6$ represents alkyl or alkenyl of at not more than 4 carbon atoms, $Q_7$ represents alkyl or alkenyl of 12 to 20 carbon atoms, $Q_8$ represents alkyl or alkenyl of 4 to 20 carbon atoms, and $D_3^{\ominus}$ represents $Cl^{\ominus}$, $CH_3$—$SO_4^{\ominus}$ or $C_2H_5SO_4^{\ominus}$, and in particular have the formula

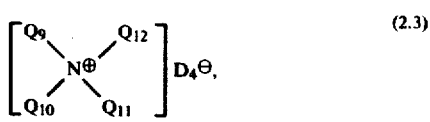
(2.3)

wherein each of $Q_9$ and $Q_{10}$ represents methyl or ethyl, each of $Q_{11}$ and $Q_{12}$ represents alkyl or alkenyl of 16 to 18 carbon atoms, and $D_4^{\ominus}$ represents $CH_3SO_4^{\ominus}$ or $C_2H_5SO_4^{\ominus}$.

$Q_1$ and $Q_2$ in formula (2) represent vinyl, allyl or in particular, methyl or ethyl, and $Q_3$ and $Q_4$ are derived in particular from saturated fatty acids, such as caprylic, lauric, palmitic, stearic, arachidic and behenic acid, and from unsaturated fatty acids, such as decenoic, oleic, linoleic and linolenic acid. In particular, technical mixtures of these fatty acids are suitable.

The aliphatic quaternary ammonium salts of the formulae (2) to (2.3), which are suitable for use as component (b) of the softening agent of the present invention, are known per se and disclosed, for example, in U.S. Pat. No. 3,954,630.

As examples of specific types of compounds of the formulae (2) to (2.3), there may be cited the compounds of one of the following formulae:

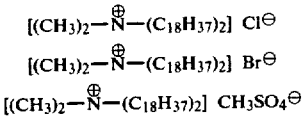 (2.4)

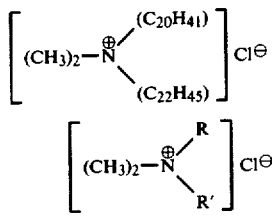 (2.5)
(2.6)
(2.7)

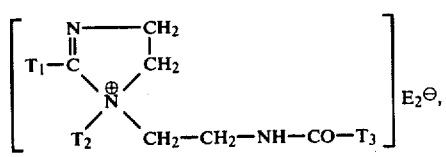 (2.8)

R,R' = 24 molar % $C_{16}H_{33}$
75 molar % $C_{18}H_{37}$
1 molar % $C_{18}H_{35}$ The compound of the formula (2.4) and, in particular, that of the formula (2.8), are especially preferred.

Mixtures of compounds of the formulae (2) to (2.8) are also possible for use as component (b) of the softening agent of the present invention.

Preferred embodiments of the imidazolinium salts of the formula (3) have the formula

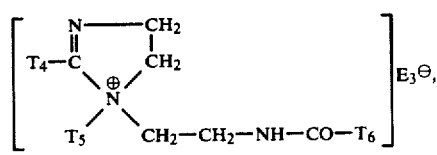 (3.1)

wherein $E_2^\ominus$ has the same meaning as $D_2^\ominus$ in formula (2.1) and $T_1$, $T_2$ and $T_3$ have the given meanings, and in particular have the formula

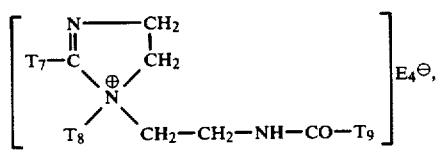 (3.2)

wherein $T_5$ has the meanings of $Q_5$ and $Q_6$, each of $T_4$ and $T_6$ has the meaning of $Q_7$, and $E_3^\ominus$ has the meaning of $D_3^\ominus$ in formula (2.2), and especially have the formula

 (3.3)

wherein $T_8$ has the meanings of $Q_5$ and $Q_{10}$, each of $T_7$ and $T_9$ has the meaning of $Q_{11}$ and $Q_{12}$, and $E_4^\ominus$ has the meaning of $D_4^\ominus$ in formula (2.3).

$T_2$ in formula (3), like each of $Q_1$ and $Q_2$ in formula (2), accordingly represents for example vinyl, allyl or, in particular, methyl and ethyl, and $T_2$ and $T_3$ are derived in particular from the fatty acids indicated for $Q_3$ and $Q_4$.

The ammonium salts of the formulae (3) to (3.3), which are suitable as component (b) of the softening agents of the present invention, are known per se and are disclosed for example in U.S. Pat. No. 3,954,634 and in British Pat. No. 1,453,296.

As examples of specific types of compounds of the formulae (3) to (3.3), the compounds of one of the following formulae may be mentioned:

 (3.4)

 (3.5)

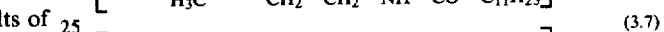 (3.6)

 (3.7)

[structure] (3.8)

R, R' = mixture of $C_{16}H_{33}$, $C_{17}H_{35}$ and $C_{17}H_{33}$

The compounds of the formulae (3.7) and, specifically, of the formula (3.8), are particularly preferred. Mixtures of compounds of the formulae (3) to (3.8) are also suitable for use as component (b) of the softening agent of the present invention.

A preferred softening agent is one that contains either the diester/amine adduct of the formula (1.14, or, in particular, of the formula 1.27), as component (a), and the aliphatic quaternary ammonium salt of the formula (2.3) or, in particular, of the formula (2.8), as component (b), or, although less preferred, the diester/amine adduct of the formula (1.14) or, in particular, of the formula (1.27), as component (a), and the imidazolinium salt of the formula (3.3) or, in particular, of the formula (3.8), as component (b).

The preferred mixture ratio of the components (a) to (b) is 9:1 to 3:7, in particular 8.5:1.5, and most particularly 8:2 to 5:5.

The softening agent of the present invention has an active substance content of components (a) and (b) of at least 10, preferably 25 to 99 and in particular 40 to 85, percent by weight, and can contain water or a lower alkanol, for example isopropanol, as well as additives, such as surfactants, emulsifiers, optionally a dye and/or fluorescent brightener, a perfume, a preservative which is derived for example from a phenol or formaldehyde, and an organic salt, for example sodium chloride and sodium sulphate.

The softening agent of the present invention can be used for a variety of purposes, for example as an after-rinse softener and an after-shampoo hair conditioner, and this utility constitutes a further object of the invention.

If the softening agent is processed to an after-rinse softener, this latter preferably contains 1 to 50, in particular 4 to 25, percent by weight of active substance of components (a) and (b). The after-rinse softener also contains water, optionally further additives, such as a lower alkanol, an inorganic salt, for example sodium chloride and sodium sulphate, a non-ionogenic surfactant, a dye and/or fluoroescent brightener, a perfume and, if desired, an antimicrobial agent.

If the softening agent is processed to an after-shampoo hair conditioner, this latter preferably contains 0.5 to 20, in particular 2 to 5, percent by weight of active substance of components (a) and (b). The hair conditioner additionally contains water and is preferably in the form of a low-viscosity to viscous emulsion. The hair conditioner can also contain further additives, such as a perservative, a dye, a perfume or, if desired, an antidandruff agent.

The methods by which the softening agent of the present invention can be applied also constitute a further object of the invention.

In the rinsing method, a preferably already washed substrate is treated with the softening agent of the invention. Organic fibrous material is in particular suitable for use as substrate. The fibrous material is usually treated with an aqueous liquor at a temperature which is dependent on the washing conditions, for example at 10° to 50° C. A soft, smooth, pleasing handle is always imparted to the treated material. Accordingly, a preferred method of application consists of a method of softening organic fibrous material, wherein the material is treated with an after-rinse softener of the present invention, preferably in the form of an aqueous liquor. The aqueous liquor usually contains, per liter, 0.5 to 3, preferably 1 to 2, g of after-rinse softener.

The organic fibrous material which is treated according to the invention can be in any stage of processing, i.e. as staple fibres, endless filaments, webs, in particular woven or knitted fabrics, dyed or undyed, treated or untreated with fluorescent brighteners, or can be in particular in the form of further processed garment fabric. The organic fibrous material is accordingly always preferably a textile material.

Suitable textile fibres are both synthetic man-made and regenerated man-made and especially natural fibres. Blends of synthetic and natural fibres are also suitable.

Examples of synthetic fibres are rayon, viscose staple fibre, viscose, cellulose diacetate and cellulose triacetate, polyacrylonitrile, acrylonitrile polymers, polyamide, in particular fibres made from poly-2-caprolactam, polyhexylmethylenediamide adipate or poly-aminoundecanoic acid and polyester, in particular fibres which are derived from terephthalic acid, for example poly-(ethylene glycol terephthalate) or poly(1,4-cyclohexylenedimethyleneterephthalate); and examples of natural fibres are linen, hemp, ramie, wool and, in particular, cotton.

Chiefly wool, polyacrylonitrile, polyamide, polyester or cotton fabrics, or woven or knitted fabrics from blends of the above fibres, can be softened according to the invention, but cotton frotté is of particular interest.

In the method of conditioning hair, preferably already washed human hair, which is advantageously still wet, is treated with the after-shampoo hair conditioner, preferably at 20° to 40° C. A soft, smooth, pleasing handle is likewise always imparted to the treated hair, for example wigs. Accordingly, a preferred method of application consists of a method of softening preferably human hair, wherein the hair is preferably treated at 20° to 40° C. with the after-shampoo hair conditioner.

In addition to the good soft-handle properties, the material treated according to the invention has, inter alia, excellent antistatic and hydrophilic properties and does not have a tendency to yellowing. If the softening agents of the invention are applied in the presence of fluorescent brighteners, good lightfast white effects are obtained on the treated materials. On treating dyed material, the light and colour fastness of the dyeings are maintained.

These positive properties make the fabric softeners and after-shampoo hair conditioners of the present invention suitable for use both in industry and in the home. The favourable ecological properties of the softening agent of the invention, in particular its low toxicity to fish, are advantageous. In addition, the softening agents of the invention are distinguished by their good compatibility with virtually all additives customarily employed in the detergent, textile and cosmetics industries.

A further and material advantage of the softening agents of the present invention resides in the fact that the components (a) and (b) contained therein do not have an additive effect on the good properties of the indicated kind which are possessed by the materials treated with the softening agents, but rather have an unexpected synergistic positive effect.

The invention is illustrated by the following Examples, in which the parts and percentages are by weight.

EXAMPLE 1

1 part of a combination the compounds of the formulae (1.26) and (2.8) and (1.26) and (3.8) respectively, is diluted with desalinated water of 60° C. so as to give at 20° C. a 1% stock solution, referred to 100% of active substance of the compound employed. The stock solutions obtained are diluted in turn with water of 10° dH in the weight ratios given in Table 1, so that the rinsing solution contains altogether 0.2 g of softening agent per liter as 100% active substance. A cotton frotté fabric with a weight per unit area of 334 g/m² and a polyacrylic fabric with a weight per unit area of 138 g/m² are treated with the rinsing solutions for 5 minutes at 25° C. and at a liquor ratio of 1:20, spin-dried, then dried at 60° C. and conditioned at 20° C. and 65% relative humidity. The individual frotté and acrylic samples are assessed manually by three assessors using handle ratings, 0 being the poorest and 4 the best rating. Each test is repeated, so that the ratings reported in Table 1 represent the average of 6 assessments.

Table 1

| weight ratio of the compound of the formula (1.26): to the compound of the formula (3.8) in the rinsing solution | Handle Ratings | | Test No. |
|---|---|---|---|
| | polyacrylonitrile | cotton | |
| 10.0 | | 0.8 | 1 |
| 5:5 | | 2.7 | 2 |
| 3:7 | | 2.7 | 3 |
| 0:10 | | 2.2 | 4 |
| weight ratio of the compound of the formula | | | |

Table 1-continued

| weight ratio of the compound of the formula (1.26): to the compound of the formula (3.8) in the rinsing solution | Handle Ratings polyacrylonitrile | Handle Ratings cotton | Test No. |
|---|---|---|---|
| (1.26): to the compound of the formula (2.8) in the rinsing solution | | | |
| 10:0 | 2 | | 5 |
|  |  | 0.75 | 6 |
| 8:2 | 2.5 | | 7 |
|  |  | 2.7 | 8 |
| 7:3 | 3 | | 9 |
|  |  | 3.2 | 10 |
| 5:5 | 2.5 | | 11 |
|  |  | 3.1 | 12 |
| 0:10 | 1.7 | | 13 |
|  |  | 2.5 | 14 |
| untreated samples | 0 | | 15 |
|  |  | 0 | 16 |

The soft-handle effects obtained in test 10 of Table 1 are compared with the soft handle effects obtained in tests 6 and 14, using the method of evaluation of J. Renard, Report of the Comité international de la détergence, Zürich III, Section C, pp. 295-304 (1972), the assessment being made by 18 persons in accordance with the principle of sequential analysis. In this comparison, the combination of the compounds in the rinsing solution of test 10 was quite unequivocally preferred to the individual compounds in the rinsing solution of tests 6 and 14, even after the first run of assessments.

Results similar to those reported in Table 1 are obtained by using acid salts of one of the formulae (1.15) to (1.25) instead of the acid salt of the formula (1.26), ammonium salts of one of the formulae (2.4) to (2.7) instead of the ammonium salt (2.8), or of imidazolinium salts of one of the formulae (3.4) to (3.7) instead of the imidazolinium salt of the formula (3.8).

EXAMPLE 2

A rinsing solution which contains the compounds of the formulae (1.26) and (2.8) is prepared as indicated in Example 1, except that 0.04% (referred to the weight of the fabric to be treated) of a fluorescent brightener of the formula

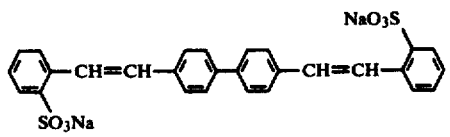

(4)

is added. A polyamide knitted fabric with a weight per unit area of 244 g/m² is treated with this rinsing solution as in Example 1. The degree of whiteness of the treated fabric is determined by spectophotometry (xenon light with D 65) according to the method of G. Anders, Textilveredlung 9 [1], 10-13 (1974), using the degree of whiteness formula of Ganz in which 0=15. The results of the measurements of the degree of whiteness are summarised in Table 2. The degree of whiteness values are desirably as high as possible. Results similar to those reported in Table 2 are obtained by using acid salts of one of the formulae (1.15) to (1.25) instead of the acid salt of the formula (1.26), or ammonium salts of one of the formulae (2.4) to (2.7), or imidazolinium salts of one of the formulae (3.4) to (3.8) instead of the ammonium salt of the formula (2.8).

Table 2

| weight ratio of the compound of the formula (1.26): to the compound of the formula (2.8) in the rinsing solution | Degree of whiteness | Test No. |
|---|---|---|
| 10:0 | 115 | 17 |
| 8:2 | 119 | 18 |
| 7:3 | 121 | 19 |
| 5:5 | 130 | 20 |
| 0:10 | 112 | 21 |

EXAMPLE 3

A rinsing solution which contains the compounds of the formulae (1.26) and (2.8) is prepared as indicated in Example 1. A polyester fabric with a weight per unit area of 127 g/m² is treated with the above rinsing solution as in Example 1, except that it is conditioned at 22° C. and 45% relative humidity. To determine the electrostatic behaviour of the treated fabric, the volume resistance is measured, the average of two measurements in each case being given in Table 3. The resistance values are desirably as low as possible.

Results similar to those reported in Table 3 are obtained by using acid salts of one of the formulae (1.15) to (1.25) instead of the acid salt of the formula (1.26), or ammonium salts of one of the formulae (2.4) to (2.7) or imidazolinium salts of one of the formulae (3.4) to (3.8) instead of the ammonium salt of the formula (2.8).

Table 3

| Weight ratio of the compound of the formula (1.26): to the compound of the formula (2.8) in the rinsing solution | Volume resistance | Test No. |
|---|---|---|
| 10:0 | $1.5 \cdot 10^{12}$ | 22 |
| 9:1 | $3.5 \cdot 10^{11}$ | 23 |
| 8:2 | $2.5 \cdot 10^{10}$ | 24 |
| 7:3 | $9 \cdot 10^{9}$ | 25 |
| 5:5 | $5.5 \cdot 10^{9}$ | 26 |
| 0:10 | $1.3 \cdot 10^{12}$ | 27 |
| untreated fabric | $10^{15}$ | 28 |

EXAMPLE 4

Aqueous emulsions are prepared which contain the amounts indicated in Table 4 of the compounds of the given formulae. Wigs of uncurled humain hair approx. 30 cm in length are wetted with water. Then 3 ml of each of the emulsions of the composition indicated in Table 4 are applied to one half of a wetted wig and rubbed into the hair by hand. The other half of the wig is treated only with water and seves as comparison. Subsequently the hair is combed briefly and then not touched in any way for 5 minutes. After this time, all the wigs are rinsed out and combed and allowed to dry under a hair drier for 30 minutes at 70° C. On combing the hair when still wet, the wet combability, and after drying, the dry combability, are assessed manually with the aid of combability ratings, 0 being the poorest and 3 the best rating. In addition, the electrostatic behaviour of the hair on being combed after drying is evaluated. The results are reported in Table 4.

Results similar to those reported in Table 4 are obtained by using acid salts of one of the formulae (1.15) to (1.25) instead of the acid salt of the formula (1.26), or ammonium salts of one of the formulae (2.4) to (2.7) or imidazolinium salts of one of the formulae (3.4) to (3.8) instead of the ammonium salt of the formula (2.8).

Table 4

| | | | formula and amount of the compounds which are contained in the emulsions for hair treatment | | |
|---|---|---|---|---|---|
| | untreated hair | (1.26) 3% | (1.26) and (2.8) 3% weight ratio (1.26) : (2:8) 7.5:2.5 | (2.8) 3% | (2.8) 1% |
| wet combability ratings | 0 | 1 | 3 | 3 | 3 |
| dry combability ratings | 0 | 0 | 3 | 2 | 1 |
| electrostatic behaviour on combing +/− * | + | + | − | − | + |
| test | 29 | 30 | 31 | 32 | 33 |

* + = pronounced "flying" of the hair (undesirable)
− = no "flying" of the hair (desired)

EXAMPLE 5

The procedure of Example 1 is carried out except that the cotton frotté is treated with a rinsing solution which contains the combination of the compounds of the formulae (1.26), (2.8) and (3.8) in the weight ratios indicated in Table 5. The handle ratings (average of 6 evaluations in each case) of the treated fabrics are also reported in Table 5. Results similar to those reported in Table 5 are obtained by using acid salts of the formulae (1.15) to (1.25) instead of the acid salt of the formula (1.26), or of a mixture of ammonium salts of one of the formulae (2.4) to (2.7) and imidazolinium salts of one of the formulae (3.4) to (3.7) instead of the mixture of the ammonium salt of the formula (2.8) and the imidazolinium salt of the formula (3.8).

Table 5

| weight ratio of the compounds of the formula (1.26):(2.8) (3.8) in the rinsing solution | Handle ratings | Test No. |
|---|---|---|
| 10 : 0 : 0 | 0.8 | 34 |
| 5 : 2.5 : 2.5 | 2.6 | 35 |
| 0 : 5 : 5 | 2.4 | 36 |

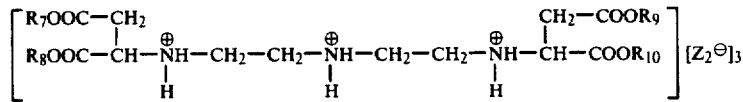

What is claimed is:

1. A softening agent which contains (a) a diester/amine adduct of the formula $$R_1-O-\overset{O}{\underset{\|}{C}}-CH_2 \quad \quad X_1 \quad X_2 \quad X_3$$
$$R_2-O-\underset{\|}{C}-CH-(CH_2)_s=\overset{|}{N}\left[A_1-\overset{|}{N}\right]_{n-1}(A_2)_{m-1}-\overset{|}{N}-Y_1,$$
$$\quad \quad \overset{\|}{O}$$

in which $R_1$ and $R_2$ each are alkyl or alkenyl of 12 to 22 carbon atoms, m and s each are 1 or 2 and n is 1, 2, 3 or 4, $A_1$ and $A_2$ each are alkylene of 2 or 3 carbon atoms or 2-hydroxy-n-propylene, $X_1$, $X_2$ and $X_3$ each are hydrogen, alkyl of 1 to 4 carbon atoms, hydroxyalkyl or hydroxy-halogenalkyl of 2 to 4 carbon atoms or are a radical of the formula $$-(CH_2)_{s'-1}-\underset{\underset{\|}{C}-OR_4}{\overset{CH_2-\overset{O}{\underset{\|}{C}}-OR_3}{\underset{|}{CH}}}$$
$$\quad \overset{\|}{O}$$

in which $R_3$ and $R_4$ each are alkyl or alkenyl of 12 to 22 carbon atoms and s' is 1 or 2, with the proviso that, if n is 3 or 4, the individual radicals $X_2$ are the same or different, and $Y_1$ is hydrogen, alkyl of 1 to 4 carbon atoms or a radical of the formula $$-(CH_2)_{s''-1}-\underset{\underset{\|}{C}-OR_6}{\overset{CH_2-\overset{O}{\underset{\|}{C}}-OR_5}{\underset{|}{CH}}},$$
$$\quad \overset{\|}{O}$$

in which $R_5$ and $R_6$ each are alkyl or alkenyl of 12 to 22 carbon atoms and s" is 1 or 2, and the ratio of the diester groups to the nitrogen atoms is 1:1 and the adduct of the indicated formula is in the form of the free base, acid salt or quaternary ammonium salt; and (b) a quaternary ammonium salt selected from the group consisting of the formula $$\left[\begin{array}{c} Q_1 \diagdown_{N^\oplus}\diagup Q_4 \\ Q_2 \diagup \diagdown Q_3 \end{array}\right] D_1^\ominus$$

and of the formula $$\left[\begin{array}{c} N \longrightarrow CH_2 \\ T_1-\underset{\|}{C} \diagdown_{\overset{\oplus}{N}} \diagup \overset{|}{CH_2} \\ T_2 \diagup \diagdown CH_2-CH_2-NH-CO-T_3 \end{array}\right] E_1^\ominus,$$

in which $Q_1$ and $T_2$ each are hydrogen, alkyl or alkenyl of at most 8 carbon atoms, $Q_2$ is alkyl or alkenyl of at most 8 carbon atoms, $Q_3$, $T_1$ and $T_3$ each are alkyl or alkenyl or alkenyl of 8 to 30 carbon atoms, $Q_4$ is alkyl or alkenyl of at most 30 carbon atoms, and $D_1^\ominus$ and $E_1^\ominus$ each are anion which imparts water-solubility or water-dispersibility to the ammonium salts, the weight ratio of diester/amine adduct to ammonium salts being 9.5:0.5 to 1:9.

2. A softening agent according to claim 1, which contains as component (a) a diester/amine adduct of the formula

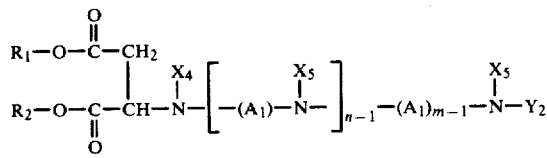

in which $R_1$ and $R_2$ each are alkyl or alkenyl of 12 to 22 carbon atoms, m is 1 or 2 and n is 1,2, 3 or 4, $A_1$ is alkylene of 2 or 3 carbon atoms or 2-hydroxy-n-propylene, $X_4$ and $X_5$ each are hydrogen, alkyl of 1 to 4 carbon atoms, hydroxyalkyl or hydroxy-halogen-alkyl of 2 to 4 carbon atoms, $Y_2$ is alkyl of 1 to 4 carbon atoms or a radical of the formula $$\begin{array}{c} \text{O} \\ \| \\ \text{CH}_2\text{—C—O—R}_3 \\ | \\ \text{—CH—C—O—R}_4 \\ \| \\ \text{O} \end{array}$$

in which $R_3$ and $R_4$ each are alkyl or alkenyl of 12 to 22 carbon atoms, said adduct being in the form of a free base, acid salt or quaternary ammonium salt.

3. A softening agent according to claim 1, which contains as component (a) a diester/amine adduct of the formula

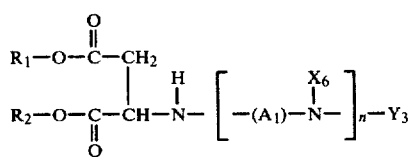

in which $R_1$, $R_2$, $A_1$ and n are as defined in claim 1, $X_6$ is hydrogen, methyl or ethyl, and $Y_3$ is methyl, ethyl or a radical of the formula

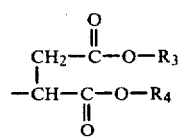

in which $R_3$ and $R_4$ are as defined in claim 1.

4. A softening agent according to claim 1, which contains as component (a) a diester/amine adduct which is in the form of an acid salt of a hydroxyalkyl- or alkylcarboxylic acid of 1 to 3 carbon atoms or of a diester of phosphorous acid.

5. A softening agent according to claim 1, which contains as component (a) a diester/amine adduct of the formula

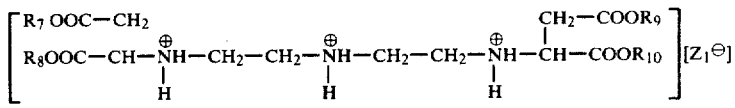

in which $R_7$, $R_8$, $R_9$ and $R_{10}$ each is alkyl or alkenyl of 16 to 18 carbon atoms and $Z_1^\ominus$ represents the radical of an acid having reductive character.

6. A softening agent according to claim 1, which contains as component (a) a diester/amine adduct of the formula

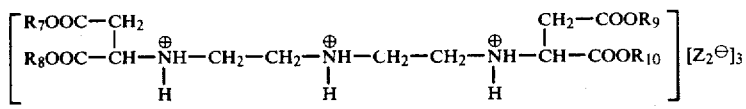

in which $Z_2^\ominus$ is $CH_3COO^\ominus$ or $HCOO^\ominus$ and $R_7$, $R_8$, $R_9$ and $R_{10}$ each is alkyl or alkenyl of 16 to 18 carbon atoms.

7. A softening agent according to claim 1, which contains as component (b) a quaternary ammonium salt selected from the group consisting of the formula

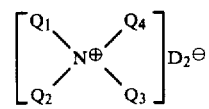

and of the formula

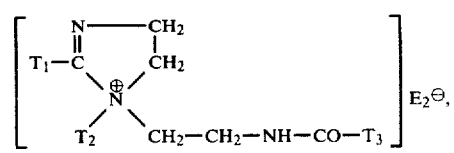

in which $D_2^\ominus$ and $E_2^\ominus$ each are the anion of a hydrohalic acid, of a dialkyl sulphate containing 1 or 2 carbon atoms in the alkyl moiety, or of an alkylcarboxylic acid of 1 to 4 carbon atoms, and $Q_1$, $Q_2$, $Q_3$, $Q_4$, $T_1$, $T_2$ and $T_3$ are as defined in claim 1.

8. A softening agent according to claim 1, which contains as component (b) a quaternary ammonium salt selected from the group consisting of the formula

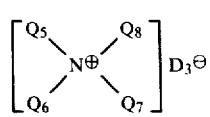

and of the formula

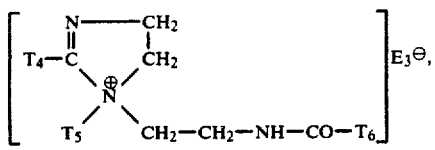

in which $Q_5$, $Q_6$ and $T_5$ each are alkyl or alkenyl of at most 4 carbon atoms, $Q_7$, $T_4$ and $T_6$ each are alkyl or alkenyl of 12 to 20 carbon atoms, $Q_8$ is alkyl or alkenyl of 4 to 20 carbon atoms, and $D_3^\ominus$ and $E_3^\ominus$ each are $Cl^\ominus$, $CH-SO_4^\ominus$ or $C_2H_5SO_4^\ominus$.

9. A softening agent according to claim 1, which contains as component (b) a quaternary ammonium salt selected from the group consisting of the formula

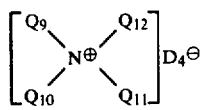

and of the formula

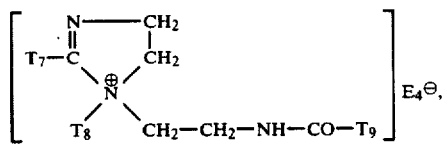

in which $Q_9$, $Q_{10}$ and $T_8$ each are methyl or ethyl, $Q_{11}$, $Q_{12}$, $T_7$ and $T_9$ each are alkyl or alkenyl of 16 to 18 carbon atoms, and $D_4^\ominus$ and $E_4^\ominus$ each are $CH_3SO_4^\ominus$ or $C_2H_5SO_4^\ominus$.

10. A softening agent according to claim 1, which contains
(a) a diester/amine adduct of the formula in which $Z_2^\ominus$ is $CH_3COO^\ominus$ or $HCOO^\ominus$ and $R_7$, $R_8$, $R_9$ and $R_{10}$ each is alkyl or alkenyl of 16 to 18 carbon atoms, and
(b) a sole quaternay ammonium salt of one of the formulae

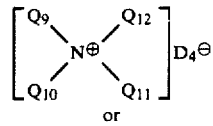

or

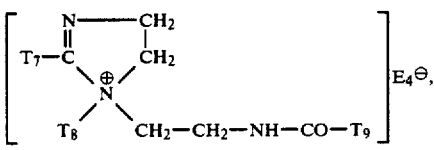

in which $Q_9$, $Q_{10}$ and $T_8$ each are methyl or ethyl, $Q_{11}$, $Q_{12}$, $T_7$ and $T_9$ each are alkyl or alkenyl of 16 to 18 carbon atoms, and $D_4^\ominus$ and $E_4^\ominus$ each are $CH_3SO_4^\ominus$ or $C_2H_5SO_4^\ominus$.

11. A softening agent according to claim 1, in which the weight ratio of diester/amine adduct to ammonium salt is 9:1 to 3:7.

12. A composition containing at least 10 percent by weight of a softening agent according to claim 1 and water or a lower alkanol.

13. A composition for use as after-rinse softener containing 1 to 50 percent by weight of a softening agent according to claim 1 and water.

14. A composition for use as an after-shampoo conditioner containing 0.5 to 20 percent by weight of a softening agent according to claim 1 and water.

15. A method of softening organic fibrous material which comprises treating said material with an after rinse softener containing a softening agent according to claim 1.

16. A method of conditioning human hair which comprises treating hair with an after-shampoo hair conditioner containing a softening agent according to claim 1.

* * * * *